(12) United States Patent
Lorenzen et al.

(10) Patent No.: US 8,707,951 B2
(45) Date of Patent: Apr. 29, 2014

(54) PROCESS FOR OPERATING A RESPIRATOR

(75) Inventors: Ralf Lorenzen, Lübeck (DE); Hans-Joachim Kohl, Lübeck (DE); Tobias Glaw, Lübeck (DE); Tilman von Blumenthal, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 1124 days.

(21) Appl. No.: 12/687,503

(22) Filed: Jan. 14, 2010

(65) Prior Publication Data
US 2010/0224189 A1    Sep. 9, 2010

(30) Foreign Application Priority Data
Mar. 6, 2009   (DE) .................. 10 2009 012 146

(51) Int. Cl.
*F16K 31/02*  (2006.01)
(52) U.S. Cl.
USPC .................................................. 128/204.21
(58) Field of Classification Search
USPC .............. 128/204.21, 204.23, 205.24, 203.14
See application file for complete search history.

(56) References Cited

U.S. PATENT DOCUMENTS

| 5,303,698    A  |         | 4/1994  | Tobia et al.            |
|-----------------|---------|---------|-------------------------|
| 5,345,930    A  | *       | 9/1994  | Cardinal et al. ......... 128/205.24 |
| 5,797,393    A  | *       | 8/1998  | Kohl ......................... 128/204.23 |
| 2005/0229926 A1 | *       | 10/2005 | Fink et al. ................ 128/200.16 |
| 2009/0293876 A1 |         | 12/2009 | Soliman et al.          |

FOREIGN PATENT DOCUMENTS

| DE | 3417954        | 11/1985 |
| DE | 694 30 693 T2  | 1/2003  |
| DE | 101 26 821     | 2/2003  |
| DE | 10347886       | 2/2005  |
| DE | 102006048680   | 9/2007  |
| JP | 10-196840      | 7/1998  |
| WO | WO 2007/142642 | 12/2007 |

* cited by examiner

*Primary Examiner* — Bhisma Mehta
*Assistant Examiner* — Jenna Zhang
(74) *Attorney, Agent, or Firm* — McGlew and Tuttle, P.C.

(57) ABSTRACT

A process for controlling a respirator with reduced gas excess, wherein a load situation (37) of an expiration valve is polled in a continuous sequence and a flow value (36) is reduced step by step from a preset starting flow value (41) and wherein the flow value (36) is again increased when a predetermined value (44) is exceeded.

21 Claims, 5 Drawing Sheets

PROCESS FOR OPERATING A RESPIRATOR

CROSS REFERENCE TO RELATED APPLICATIONS

This application claims the benefit of priority under 35 U.S.C. §119 of German Patent Application DE 10 2009 012 146.3 filed Mar. 6, 2009, the entire contents of which are incorporated herein by reference.

FIELD OF THE INVENTION

The present invention pertains to a process for operating a respirator. A form of respiration, which feeds breathing air to the patient with an imposed modulated alternating oscillation, is used for the artificial respiration of patients, especially newborn and premature babies.

BACKGROUND OF THE INVENTION

Improved ventilation of areas of the lung and hence improved oxygen/carbon dioxide gas exchange in the blood circulation of the patient are brought about by the modulated alternating oscillation of the respiration pressure without increasing the basic level of the respiration pressure. This form of respiration is called high-frequency respiration, hereinafter called HF respiration for short. The physiological respiration of an adult is typically in the range of 9 to 18 breaths per minute, and this leads to a respiration rate of 0.15 Hz to 0.3 Hz. A premature or newborn baby breathes at a rate of 60 to 120 breaths per minute, which corresponds to a respiration rate of 1 Hz to 2 Hz. The modulated frequency of high-frequency respiration, hereinafter called HF frequency, is in the range of 5 to 20 oscillations per second, i.e., markedly above the physiological respiration rates. At the outlet of the HF respirator, the HF respiration continuously generates oscillations of the pressure amplitude, which follow the HF frequency, which are superimposed to a physiological alternation of inspiration and expiration and a mean airway pressure. The HF frequency, the mean airway pressure, the pressure amplitude of the HF oscillation and the I:E (Inspiratory: Expiratory) ratio, which corresponds to the ratio of the duration of inspiration to the duration of expiration, are sent as input parameters to a control and regulating unit for controlling and regulating the mode of operation of HF respiration.

This input parameter comprising the frequency, pressure amplitude, mean airway pressure and I:E ratio is derived by the user from therapeutic considerations and the patient's constitution and can be set by the user as direct set points on an operating unit, on the one hand, and, in another variant, the set points can also be derived from other parameters. A process of how the HF frequency and the pressure amplitude of the HF oscillation can be derived from a set tidal volume is described in DE 102006048680 B3. WO 2007142642 A1 describes a process for controlling pressure fluctuations at the rhythm of a modulated HF frequency for a respirator. A respirator for use of the HF respiration is described in DE 3417954 A1, wherein a sine-like alternating pressure amplitude is admitted to the patient feed line in the rhythm of the HF frequency by means of a generator in conjunction with a valve arrangement and a negative alternating pressure amplitude is generated by means of a suction nozzle by actively drawing out the expiration air. The patient feed line connects the respirator to the patient, into whose lungs the pressure change oscillation is then introduced by means of an endotracheal tube or a breathing mask. The control and regulating unit converts the input parameters HF frequency, mean airway pressure, pressure amplitude and I:E ratio into the necessary manipulated variables for the pressure and flow regulation and actuation of the components of the device, for example, the suction nozzle and the valve arrangement. To generate a pneumatic pressure change oscillation at the patient, an air volume must be displaced through the patient feed line towards the patient and then away again. The patient feed line represents a dynamic pneumatic resistance for the amount of air fed, which resistance can be described by a low-pass filter. It results from this that to send a pressure change oscillation to the patient with increasing frequency, the flow velocities necessary for this increase superproportionally.

To avoid additional pneumatic resistances and volumes in the gas feed line at the patient's mouth and pressure drops resulting therefrom, sensor systems located near the patient for detecting the flow rate are dispensed within HF respiration in many cases. To adequately provide diverse possibilities of combination of variation of the pneumatic parameters, e.g., resistance and compliance, for different types of patients and different tube systems, with the HF respiration, the HF respirator is operated with excess gas volume and with a flow velocity resulting therefrom in order to ensure the intended and set pressure change amplitude and HF frequency at the patient in all cases. Due to this operation with gas excess, the metered quantity of gas is greater than is necessary for the respiration settings.

SUMMARY OF THE INVENTION

The object of the present invention is to propose a process for the consumption-adapted metering of a quantity of gas for a respirator.

According to the invention, a process is provided for controlling a respirator with an expiration valve. The process comprises reducing a flow value step by step from a preset starting flow value by a first increment and determining a load situation of the expiration valve. An exceeding of a first threshold value of the load situation of the expiration valve is monitored. Upon the first threshold value of the load situation being exceeded the process proceeds with one of:

increasing the flow value by a second increment; and not further reducing the flow value further, monitoring an exceeding of a second threshold value of the load situation of the expiration valve and increasing the flow value by a second increment when the second threshold value of the load situation of the expiration valve is exceeded.

According to another aspect of the invention, a process is provided for controlling a respirator with an expiration valve, the process comprises reducing a flow value step by step, determining a load situation of the expiration valve and maintaining a load situation of the expiration valve in a tolerance range.

A respirator, which is equipped for carrying out HF respiration, comprises actuators, sensors and control elements. Such a device may be a respirator equipped especially for respiration with HF respiration, a so-called HF respirator, but it may also be a respirator that is additionally equipped, besides for respiration with the usual respiration rates of 0.15 Hz to 0.3 Hz for adult patients and of 1 Hz to 2 Hz for newborn and premature babies, such that pressure oscillation respiration can be applied in the range of 5 to 20 oscillations per second as a special form of HF respiration. The components necessary for HF respiration include an inspiration valve or an air source, for example, in the form of a blower drive, an expiration valve, a suction nozzle (ejector), an input unit for inputting the parameters, and a control and regulating unit for controlling the respiration in terms of the modes of operation and forms of respiration. Further components are the gas mixture, gas metering, flow regulation, flow measurement, pressure regulation, pressure measurement, valve actuation and components for monitoring a state of the expiration valve. The suction nozzle may be operated and controlled separately or the operation and control of the suction nozzle may take place in combination with the respiration control, the control of the HF respiration, the pressure and flow regulation. Uncontrolled operation of the suction nozzle brings about continuous removal of a quantity of air in the expiration branch of the respirator. This quantity of air must be delivered by the respirator for the inspiration as a quantity of fresh gas. It is also possible to carry out an HF respiration with positive pressure change amplitude, in principle, without a suction nozzle, but negative pressure change amplitude cannot be applied with such an embodiment. The set of parameters comprising the frequency, pressure amplitude, mean airway pressure and I:E ratio, which is transmitted via the input unit, arises from the therapeutic considerations of the user taking the patient's constitution into account and this set of parameters presets standards for the operation of HF respiration. Preset standards for the pressure and preset standards for the flow rate, which are transmitted by the respiration control to the expiration valve and result in the preset form of respiration, can be determined from these standards. A sine-shaped positive pressure change amplitude is imposed to the inspiration air in conjunction with the switched expiration valve and the inspiratory gas metering, embodied as a switched inspiration valve or as a blower drive, and a negative pressure change amplitude is generated by actively drawing out the expiration air by means of the suction nozzle. The process according to the present invention performs a lowering of the preset flow values in a cyclical and/or continuous manner and uses the state of the expiration valve in a closed control loop as a feedback in the closed loop.

Possibilities of monitoring the states of valves and valve arrangements are known from the state of the art; for example, the monitoring of a metering valve and of a shut-off valve is described in DE 10347886 B3. The control of a valve with a valve closing means by means of detection and control engineering feedback of the valve closing velocity is described in DE 10126821 C1. In a first embodiment of the process for the consumption-adapted metering of a quantity of gas for a respirator, the set points for the form of respiration, metering of the rate of flow, set points for the inspiration and expiration valves are determined from the standards for the HF respiration in the control and regulating unit and passed on to the actuators and components and the HF respiration operation is begun. These set points are selected to be such that the gas metering has a gas excess in relation to the pressure amplitudes of the HF respiration, which are to be regulated. A stepwise lowering of the rate of flow is performed in the first step in a first continuous loop in each respiration cycle of the artificial respiration with a first increment in order to reduce the gas excess. The state of the expiration valve is determined in the next step. The stepwise lowering of the rate of flow is continued in the first continuous loop in a first embodiment until the state of the expiration valve determined exceeds a first predetermined limit value. The limit value arises from the fact that the expiration valve operates with excessively increased mechanical load in case of lack of gas to generate the pressure change amplitudes in an operating state. When the first predetermined limit value of the expiration valve is exceeded, the rate of flow is again increased with a second increment. The state of the expiration valve can be detected in the sense of the present invention continuously or also cyclically at discrete points in time.

The reduction and increase in the rate of flow can be carried out at the points in time at which the change takes place between two consecutive respiration cycles. Besides this variant, the present invention also covers the reduction and increase in the rate of flow during a current respiration cycle or between two consecutive respiration cycles. Furthermore, the present invention also covers a variant in which an increase or reduction of the rate of flow is performed after waiting for a predetermined number of respiration cycles without an increase or reduction of the rate of flow or a variant in which an increase or reduction of the rate of flow is carried out asynchronously from the respiration cycle. The load of the expiration valve is again reduced hereby and is subsequently again below the first predetermined limit value. The first continuous loop is subsequently continued with a jump into the first step. A second continuous loop, in which the desired standards for the HF respiration and changes in the desired standards are polled by the user and passed on to the control and regulating unit, is superimposed to the first continuous loop.

In a second variant according to the present invention, the second increment is reduced in the course of respiration each time the first predetermined limit value of the expiration valve is exceeded with a subsequent increase in the rate of flow by this second increment. The valve situation is thus brought closer to the first predetermined limit value without having to accept a great fluctuation of the rate of flow. The second increment is reduced only to the extent given by the dimensioning of the first increment. A practical value for a mutual adaptation of the rate of flow and the valve situation, which is optimized over time, is obtained for the second increment with a value of 50% to 150% of the first increment. The reduction of the second increment is interrupted in case the first predetermined limit value continues to be exceeded and is again continued as soon as a lowering of the flow rate with the first increment has not caused any exceeding of the predetermined first limit value in the further course.

As an alternative to increasing the rate of flow if the first predetermined limit value is exceeded, the rate of flow may also be maintained at this first limit value in a third embodiment of the present invention. The rate of flow is then increased as soon as a second predetermined limit value is exceeded. The valve is operated in this manner in a corridor between the first and second limit values.

In a special expansion of the second and third embodiments, the first and second increments are changed from the preset starting values in the course of respiration by a regulation in which the valve monitoring unit is designed as a regulator, by which the load situation of the expiration valve is maintained in a tolerance range. The current load situation of the expiration valve is now sent to the regulator in a closed loop as an actual value and a limit value of the load situation as a set point. The regulator outputs at its output a value for the first and/or second increment corresponding to its variable gain and control characteristic, with which the rate of flow is then increased or decreased in the closed loop continuously and the load situation of the expiration valve is maintained within the standard. The regulator is preferably designed here as a PI controller with proportionally and integrally acting control characteristic in order to minimize the deviation and to maintain the load situation in the corridor between the first and second limit values in the sense of the expansion according to the third embodiment or in order to maintain the load situation of the expiration valve below the first limit value with a small variation in the sense of the expansion according to the second embodiment.

In a fourth embodiment according to the present invention, the desired set point of the expiration valve is used as an input variable for the state of the expiration valve in order to determine the state of the expiration valve. The desired set point is obtained indirectly as the desired current intensity for energizing the expiration valve from the desired standards for the frequency, pressure amplitude, mean airway pressure and the I:E ratio based on the pressure measurement and pressure regulation and is available in the control and regulating unit. The pressure regulation transforms the pressure set points into the valve-specific variable of the closing force correlated with the pressure set point and the magnetization field intensity necessary for the closing force. Combined with the valve-specific properties "number of turns" and "inductance" the desired current intensity is obtained from this. The desired current intensity is analyzed in the control and regulating unit taking into account the boundary conditions for reliable operation of the expiration valve, such as the maximum exciting current, the maximum on time and the maximum valve temperature. If the desired current intensity exceeds a predetermined desired current threshold value, this is interpreted as an exceeding of the first predetermined limit value of the expiration valve and the rate of flow is increased as a consequence of this according to the present invention in the first continuous loop.

In a fifth embodiment, the actual current intensity for exciting the expiration valve is measured and detected and used as an input variable for the state of the expiration valve in order to determine the state of the expiration valve, which state is updated after the lowering of the rate of flow.

In a sixth embodiment, the winding resistance of the expiration valve is measured and detected during the operation and is used as a state variable for the state of the expiration valve in order to determine the state of the expiration valve. The winding resistance is an indicator of the heating of the expiration valve relative to a reference resistance in case of a non-energized coil based on the temperature dependence of the winding material.

In a seventh embodiment, the mutual induction voltage of the exciting coil of the expiration valve is measured and detected and used as an input variable for the state of the expiration valve in order to determine the state of the expiration valve.

In an eighth embodiment, the resulting valve temperature is imaged via a model, which includes the relationships between the mode of construction of the valve and the exciting current and also takes these relationships into account under the boundary conditions for the reliable operation of the expiration valve relative to the maximum allowable operating temperature.

In a ninth embodiment, the valve temperature is detected with a temperature sensor and is also taken into account under the boundary conditions for the reliable operation of the expiration valve. In a tenth embodiment, the ambient temperature is also included in the evaluation of the state of the expiration valve.

The ten embodiments represent independent solutions according to the present invention for reducing the quantity of gas by means of a valve state monitoring, on the one hand. Any possible combination of the ten embodiments with one another leads to an improvement of the quality of monitoring of the expiration valve and is also covered by the embodiments described and shown.

In another embodiment of the present invention, the starting flow value is derived from the set of parameters comprising the frequency, pressure amplitude, mean airway pressure and I:E ratio or even from changes of the set of parameters. Thus, using a linear assignment rule, a flow rate of 30 L/minute is obtained in a variant of this additional embodiment at a respiration rate of 5 Hz, a flow rate of 60 L/minute is obtained at a respiration rate of 10 Hz, and a flow rate of 120 L/minute is obtained at a respiration rate of 20 Hz.

In another variant of the present invention, the first increment of lowering of the rate of flow is derived from the set of parameters comprising the frequency, pressure amplitude, mean airway pressure and I:E ratio or even from changes of the set of parameters. Thus, the first increment can be derived in a preferred embodiment of this additional variant as a percentage from a current value or from a mean value of the rate of flow. A practical value for the percentage-based derivation is, for example, a value of 10% of the rate of flow. To avoid very small increments, the value of 10% may be combined with a fixed minimum increment of, for example, 1 L/minute.

In another variant of the present invention, the second increment of the increase in the rate of flow is derived from the set of parameters comprising the frequency, pressure amplitude, mean airway pressure and I:E ratio. Thus, the second increment can be derived in a preferred embodiment of this additional variant as a percentage from a current value of the rate of flow. A practical value for the percentage-based derivation is, for example, a value of 10% of the rate of flow. To avoid very small increments, the value of 10% may be combined with a fixed minimum increment of, for example, 1 L/minute.

In another preferred embodiment, the second increment of the increase in the rate of flow may be derived from the current distance between the load state of the valve and the predetermined first limit value.

In another embodiment, the first increment of the increase in the rate of flow may be derived from the current distance between the load state of the valve and the predetermined limit value.

In a special variant of this additional variant of the present invention, the second increment of the increase in the rate of flow is derived from the first increment and/or the current course of the second increment and is adapted in the further sequence of the respiration cycles.

Exemplary embodiments of the present invention are shown in the drawings and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
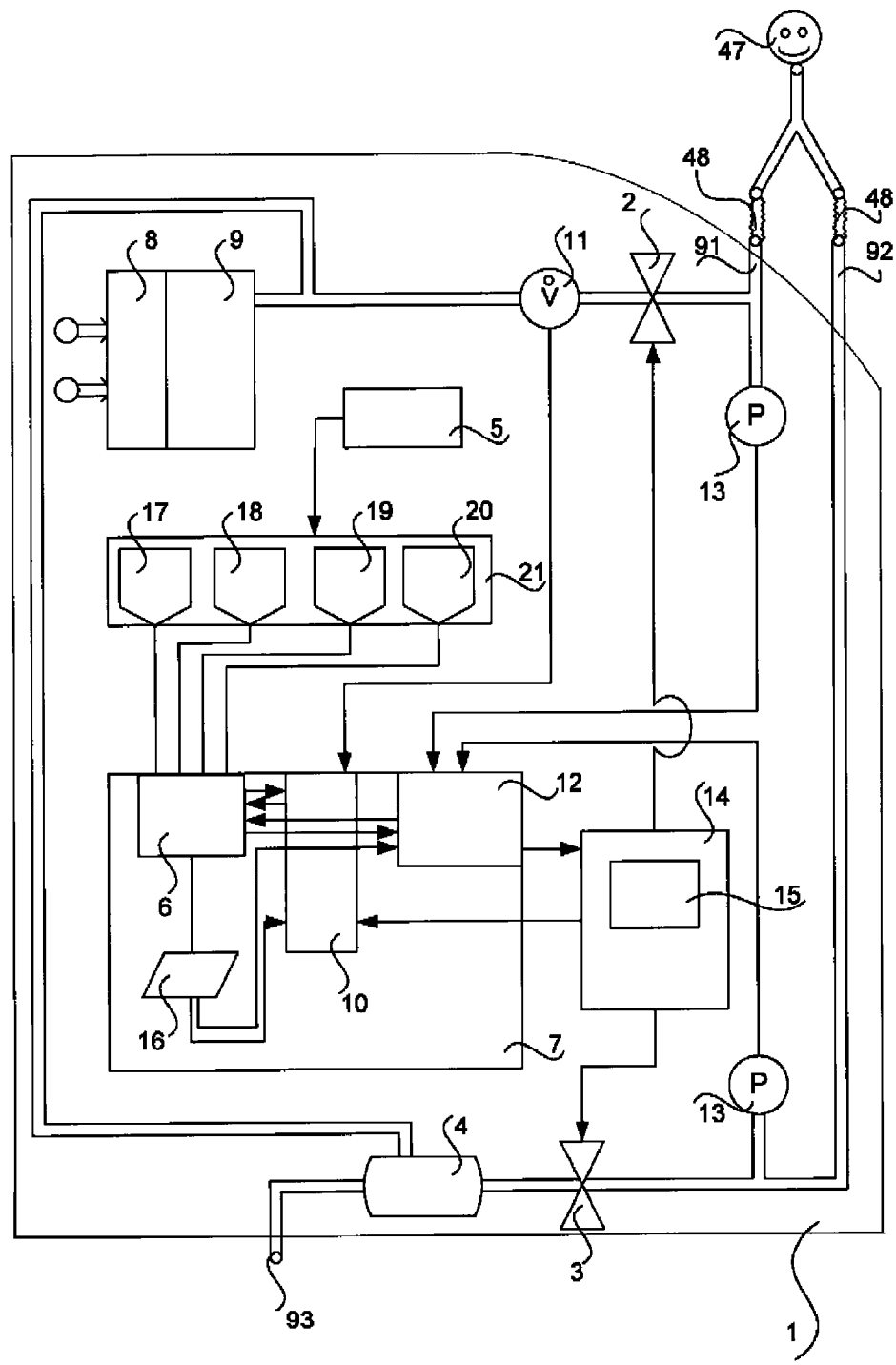
FIG. 1 is a schematic overview of the components of a respirator for HF respiration.

Referring to the drawings in particular, FIG. 1 shows a schematic overview of the components of a respirator, which is equipped for carrying out HF respiration. The respirator 1 comprises the components: an inspiration valve 2, an expiration valve 3, a suction nozzle 4, an input unit 5, a control and regulating unit 7, a gas mixing unit 8, a gas metering unit 9, a flow control 10, a flow measuring unit 11, a pressure regulating unit 12, a pressure measuring unit 13, a valve actuating unit 14, a valve monitoring unit 15, an inspiratory gas port 91, an expiratory gas port 92 and a gas outlet 93. Furthermore, a manipulated variables input 6 is present, by means of which the manipulated variables 17, 18, 19, 20 relevant for the high-frequency respiration reach as a set of parameters 16 the pressure regulating unit 12 and the flow regulating unit 10 in the control and regulating unit 7. The input unit 5 for inputting the parameters is designed such that it is provided with a user interface and represents the manipulated variables input 6 for the four manipulated variables 17, 18, 19, 20. The four manipulated variables 17, 18, 19, 20 are: The set point of the frequency for high-frequency respiration ($f_{F\text{-}ventilation}$) as a first manipulated variable 17, the pressure amplitude ($P_{amplitude}$) as a second manipulated variable 18, the mean airway pressure (MAP) as a third manipulated variable 19, and the I:E ratio ($Ratio_{I:E}$) as a fourth manipulated variable. These manipulated variables frequency 17, pressure amplitude 18, mean airway pressure 19 and I:E ratio 20 are used as desired standards 21 for the beginning and the performance of the HF respiration. The flow regulating unit 10, pressure regulating unit 12 and manipulated variable input 6 are closely connected to the control and regulating unit 7. The control and regulating unit 7 transmits the control commands to the valve control 14 and receives the desired standards 21 from input unit 5. The valve monitoring unit 15 is designed as a basic component of the valve actuating unit 14 and sets an increase in the rate of flow or a reduction of the rate of flow. The rate of flow can be set in the sense of the present invention by preset increments, on the one hand, and, on the other hand, variable increments are obtained in one embodiment in which the load situation of the expiration valve 3 is included in a closed loop. The valve monitoring unit 15 is designed in such an embodiment as a valve regulating unit with a regulator. The patient 47 is connected via a inspiratory gas port 91 and an expiratory gas port 92 to the HF respirator 1 by means of feed lines 48, in this case via a tube system. The expired air is drawn out of the feed lines 48 via a suction nozzle 4 and escapes into the environment via a gas outlet 93.

Figure 2:
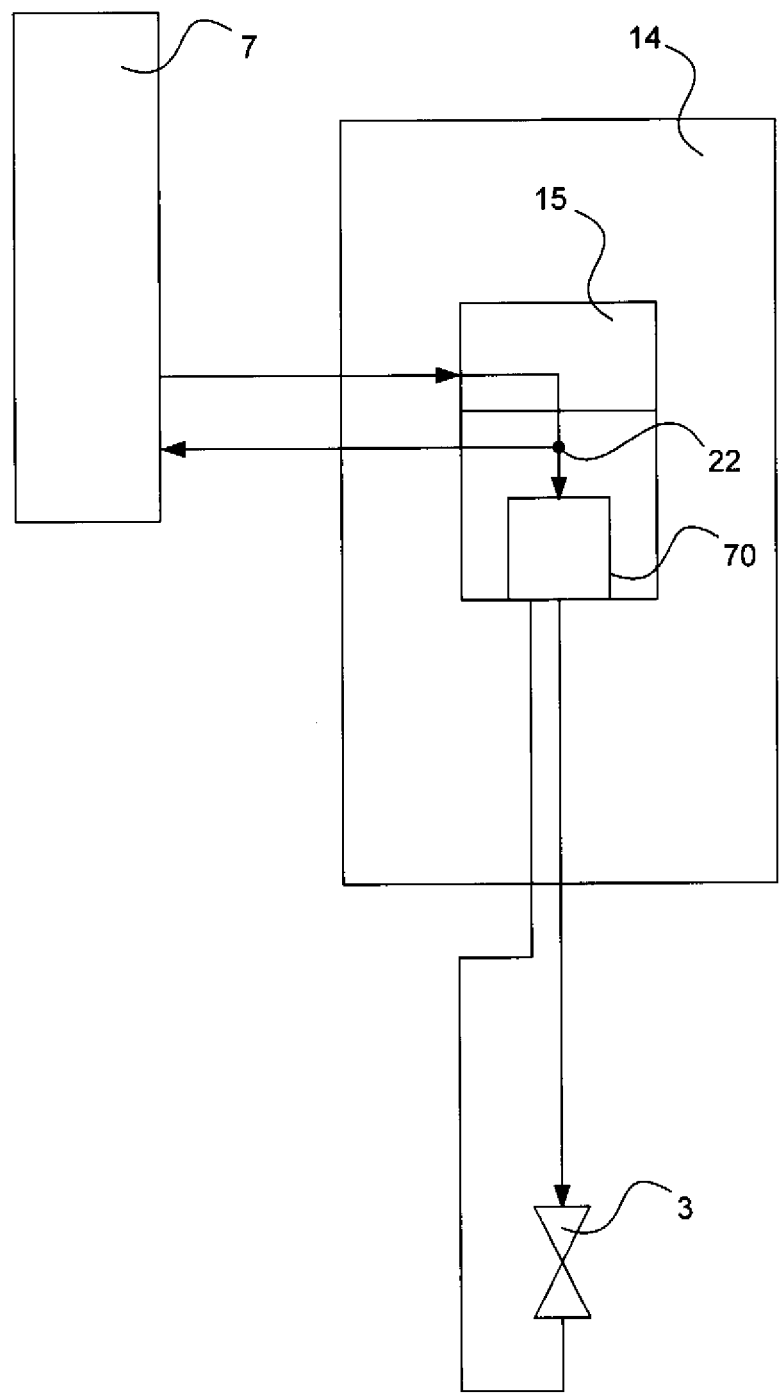
FIG. 2 is first view of the expiration valve monitoring.

FIG. 2 shows a first view of the valve control 14 and expiration valve monitoring unit 15 according to FIG. 1. Identical components are designated by the same reference numbers as in FIG. 1. According to the first embodiment according to the present invention, the set point at the input of a first final control element 70 of the expiration valve 3 and the desired current intensity ($I_{ex\text{-}v\_set}$) 22 are used in the control and regulating unit 7 as an input variable for the current state and the load situation of the expiration valve 3.

Figure 3:
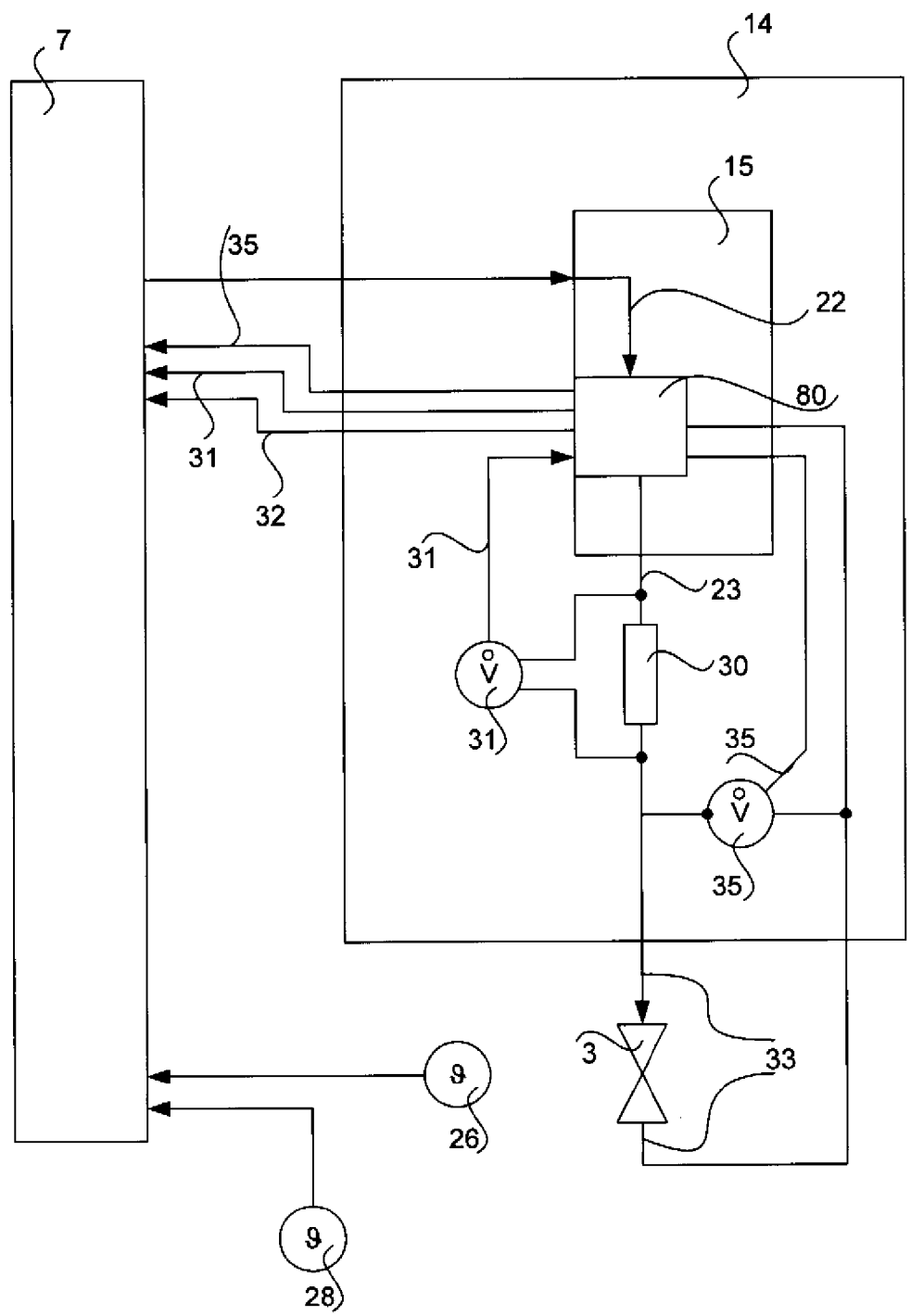
FIG. 3 is a second view of the expiration valve monitoring.

FIG. 3 shows a second view of the valve control 14 and of the expiration valve monitoring unit 15 according to FIG. 1. Identical components are designated by the same reference numbers as in FIG. 1. According to the second embodiment, the desired current intensity ($I_{ex\text{-}V\_set}$) 22 is sent to the input of a second final control element 80 by the control and regulating unit 7 for actuating the expiration valve 3. The valve current ($I_{ex\text{-}V\text{-}actual}$) 23 flowing through the windings of the valve is measured and made available for the control and regulating unit 7. The valve current ($I_{ex\text{-}V\_actual}$) 23 is detected on a precision resistor 30 as a first measured voltage 31 by means of a voltmeter in the valve control 14 and transmitted to the control and regulating unit 7.

In a first, expanded variant, the current voltage ($V_{ex\text{-}V}$) 33 is detected by means of a second voltmeter 35 at the coil of the expiration valve 3 and made available to the valve control 14.

If the current voltage ($V_{ex\text{-}V}$) 33 is detected at the moment at which the expiration valve 3 is switched on, this current voltage ($V_{ex\text{-}V}$) 33 is an indicator of the mutual induction voltage of valve 3. According to the fourth embodiment, the mutual induction voltage 35 of the expiration valve 3 is used as an input variable for the current state and the load situation of the expiration valve 3 and is transmitted to the control and regulating unit 7.

In a second, expanded variant, the combination of the current voltage ($V_{ex\text{-}V}$) 33 and the valve current ($I_{ex\text{-}V\_actual}$) 23 is used to calculate a winding resistance ($R_{ex\text{-}V}$) 32 in the valve control 14. The winding resistance ($R_{ex\text{-}V}$) 32 is a direct indicator, based on the temperature dependence of the winding material, of the heating of the coil of the expiration valve 3 and reflects the load situation of the expiration valve 3 relative to a predetermined reference value of the winding resistance 32.

The winding resistance 32 of the expiration valve 3 is used as an input variable for the current state and the load situation of the expiration valve 3 and is transmitted to the control and regulating unit 7.

Furthermore, a first temperature sensor 26 for monitoring the temperature of the expiration valve 3 is arranged in FIG. 3, which said temperature sensor can be used, alone or in connection with a second temperature sensor 28, to monitor the state of the expiration valve 3.

Figure 4:
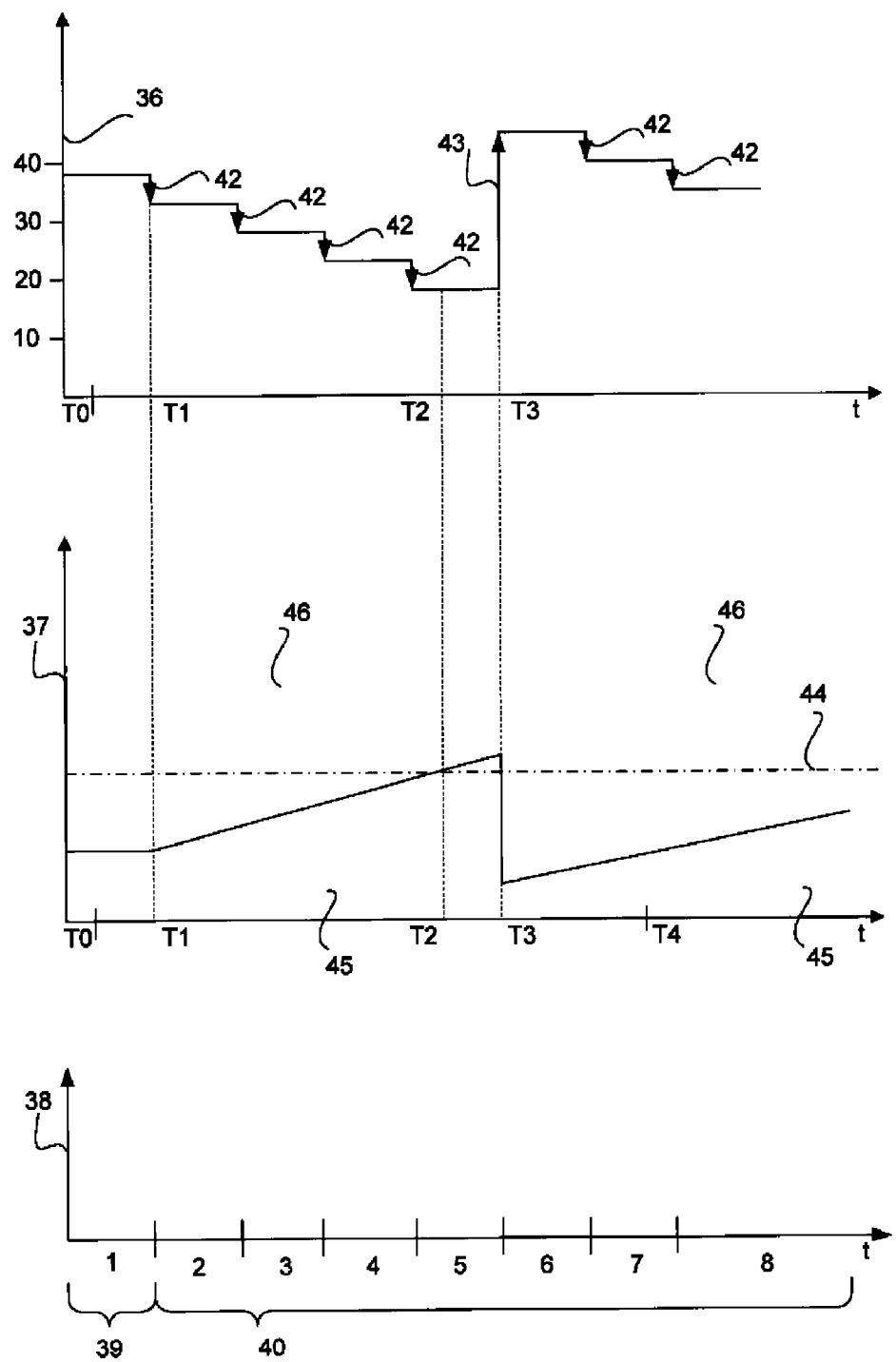
FIG. 4 is a first view of a time curve of the adaptation of the rate of flow as a function of the state of the valve.

FIG. 4 shows as an example a first view of a time curve of the flow set points 36 and a curve describing the valve states 37 in the course of respiration cycles 38. In a first respiration cycle 39, the HF respiration starts at time T0 with excess rate of flow; the starting flow value 41, equaling 38 L/minute, is above the minimum rate of flow that is necessary for maintaining the desired standards 17, 18, 19, 20 (FIG. 1). The valve state 37 is within a permissible range 45. In the course of the next respiration cycles 40, the rate of flow is reduced by a first increment of 5 L/minute at time T1 in the next respiration cycle. The first increment 42 is in the range of 1 L/minute to 20 L/minute. Valve state 37 remains within the permissible range 45 for the next three respiration cycles of the sequence of respiration cycles 40 despite the lowering below the preset first threshold value 44. During the fifth respiration cycle of the sequence of respiration cycles 40, valve state 37 exceeds the preset first threshold value 44 in a nonallowable range 46 at time T2. The rate of flow is increased thereupon in a sixth respiration cycle 40 at time T3 by an increment of 30 L/minute. The second increment 43 is in the range of 10 L/minute to 100 L/minute. Valve state 37 is now again below the preset first threshold value 44 in the allowable range. In a seventh respiration cycle of the sequence of respiration cycles 40, the rate of flow is lowered by a first increment of 5 L/minute at time T4. Valve state 37 continues to be below the preset first threshold value 44 in the allowable range 45. This curve is continued continuously in time for controlling the HF respiration. This exemplary curve shows the saving of gas. In a sequence of seven respiration cycles 39, 40, the flow rate 36 can be lowered via the feedback based on the valve state 37 from a starting value of about 38 L/minute to an average value in the range of slightly above 20 L/minute. This leads to a savings of approximately 30% to 50% of gas for this example. The selection of the first increment 42 at 5 L/minute and the selection of the second increment 43 at 30 L/minute are examples. If the second increment 43 is selected, as in this example, to be greater than the first increment 42 when dimensioning the increments 42, 43, the valve load 37 rapidly returns into the allowable range 45.

In a variant of increment adaptation, not shown in this FIG. 4, the second increment 43 is reduced during the continuation of the continuous curve to a value of 25 L/minute at the time of the next necessary increase in the rate of flow. This makes it possible for the valve load to approach the allowable range 45 with a simultaneous reduction of variations in the metering of the rate of flow. The reduction of the second increment 43 is again abolished in the further course as soon as an increase in the rate of flow by the second increment 43 fails to lead to a reduction of the valve load 37 below the first threshold value 44 into the allowable range 45. The second increment 43 is again set back in this case to the value stored in the desired standard 21.

Another variant for increment adaptation, not shown in the time curve in FIG. 4, is possible on the basis of the distance from the first threshold value 44; the greater the distance of the valve situation in the nonallowable range 46 from the first threshold value 44, the broader can the second increment 43 thus be selected to be. In case of extreme changes in the load situation, which are caused by variations of respiration, for example, by changes made by the user in the respiration rate, I:E ratio or mean airway pressure, this makes possible a rapid return into the allowable range 45.

Figure 5:
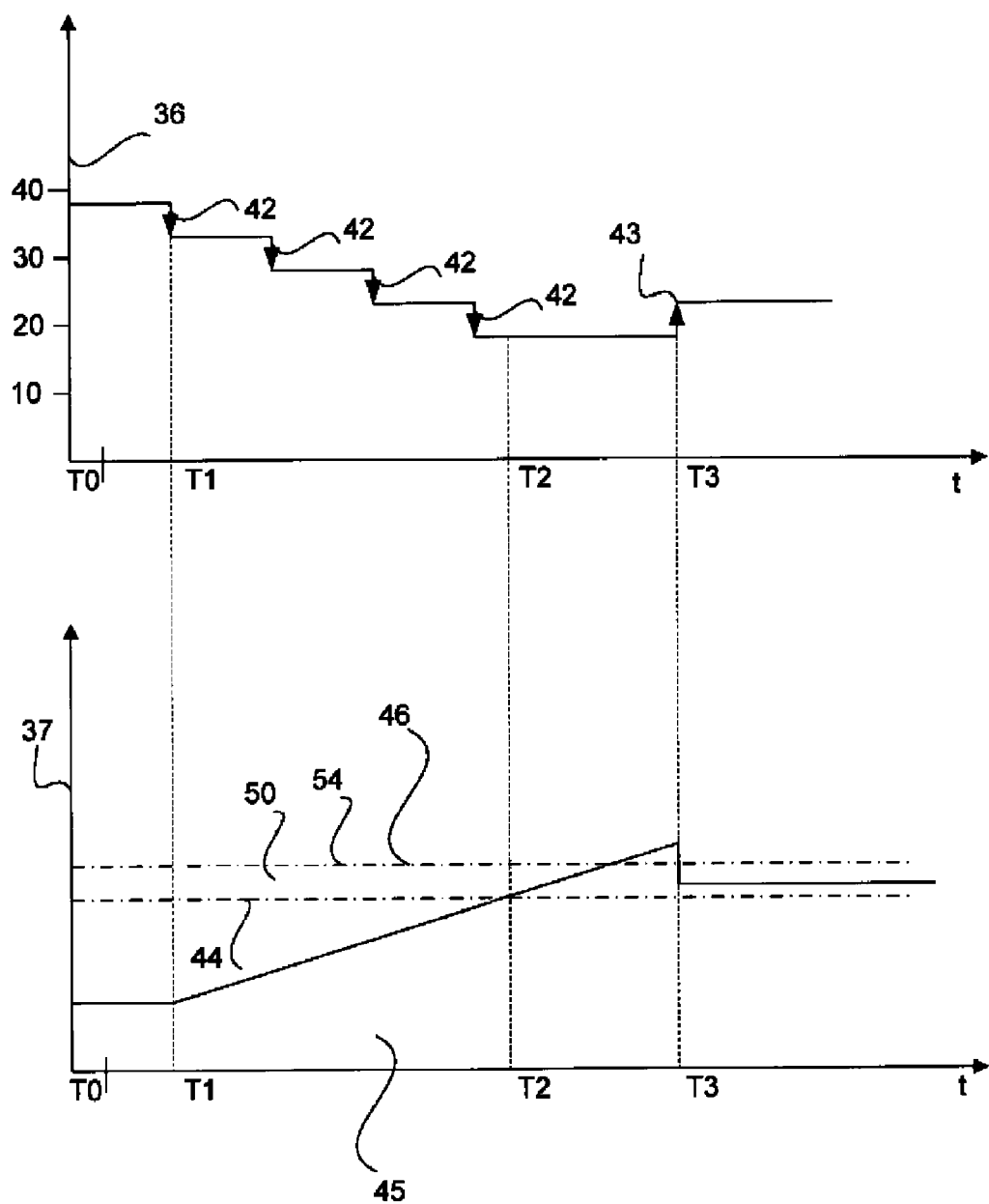
FIG. 5 is a second view of a time curve of the adaptation of the rate of flow as a function of the state of the valve.

FIG. 5 shows as an example a second view of a time curve of the flow set points 36 and of a valve state curve 37. The HF respiration starts at time T0 with an excess of rate of flow, the starting flow value 41, equaling about 38 L/minute, is above the minimum rate of flow necessary for maintaining the desired standards 17, 18, 19, 20 (FIG. 1). The valve state is checked at preset time intervals in the further course of time and the rate of flow is adapted. The preset time intervals are synchronized with the respiration control, and the adaptation takes place synchronously with each respiration cycle or synchronously with a plurality of several respiration cycles. A value suitable for practice for regulating the valve load is in the range of one to five breath cycles, proportionally adapted to the respiration rate set. The time curve begins with time T0 and the rate of flow is lowered step by step until the valve state exceeds a preset first threshold value 44.

The rate of flow is lowered by a first increment of 5 L/minute at time T1. The first increment 42 is in the range of 1 L/minute to 20 L/minute. The valve state 37 remains within the allowable range 45, below the preset first threshold value 44, despite three more subsequent steps of lowering. At time T2, the valve state 37 exceeds the preset first threshold value 44 into the nonallowable range 46. The rate of flow is not lowered further thereafter, but is maintained at this level in a tolerance range 50 above the first threshold value 44 until a second threshold value 54 is exceeded. The exceeding of the second threshold value is not caused in the course of the process directly by a further lowering of the rate of flow, but arises from variations of respiration, for example, by the changes made by the user in the respiration rate, I:E ratio or mean airway pressure. Such changes may lead to the second threshold value 54 to be exceeded. After exceeding the second threshold value 54 into the nonallowable range 46, the rate of flow is increased by a second increment at time T3 in this example. Since the valve state shall be maintained in the tolerance range 50 in this embodiment variant of the present invention, it is meaningful to set the second increment 43 in a manner similar to that in which the first increment 42 was set. The second increment 43 is thus in the range of 1 L/minute to 20 L/minute. The valve state 37 is now again in the allowable range 50 below the preset second threshold value 54. The course of reduction of the rate of flow is continued continuously over time for controlling the HF respiration as soon as the rate of flow drops below the first threshold value 44.

While specific embodiments of the invention have been described in detail to illustrate the application of the principles of the invention, it will be understood that the invention may be embodied otherwise without departing from such principles.

APPENDIX

List of Reference Numbers

1 Respirator
2 Inspiration valve
3 Expiration valve
4 Suction nozzle
5 Input unit for inputting parameters
6 Manipulated variable input
7 Control and regulating unit for controlling the respiration
8 Gas mixing unit
9 Gas metering unit
10 Flow regulation
11 Flow measurement
12 Pressure regulation
13 Pressure measurement
14 Valve actuation
15 Valve monitoring unit, valve regulating unit
16 Set of parameters
17 First manipulated variable
18 Second manipulated variable
19 Third manipulated variable
20 Fourth manipulated variable
21 Desired standard
22 Desired current intensity
23 Actual current intensity
26 First temperature sensor
28 Second temperature sensor
30 Precision resistor
31 First voltmeter
32 Winding resistance
35 Second voltmeter
36 Flow set point curve
37 Valve state curve
38 Respiration curve
39 First respiration cycle
40 Subsequent respiration cycles
41 Starting flow value
42 First increment
43 Second increment
44 First threshold value
45 Allowable range
46 Nonallowable range
47 Patient
48 Feed lines/tube system
50 Tolerance range
54 Second threshold value
70 First final control element
80 Second final control element
91 Inspiratory gas port
92 Expiratory gas port
93 Gas outlet

What is claimed is:

1. A process for controlling a respirator with an expiration valve, the process comprising:
providing a respiration flow with a preset starting rate of flow;
providing an alternating pressure amplitude to the respiration flow in the rhythm of a high frequency by control actions including controlling the expiration valve;
reducing a rate of flow step by step from the preset starting rate of flow by a first increment;
determining a load situation of the expiration valve;
monitoring an exceeding of a first threshold value of the load situation of the expiration valve; and when the first threshold value of the load situation is exceeded one of:
increasing the rate of flow by a second increment; and
not reducing the rate of flow further, monitoring an exceeding of a second threshold value of the load situation of the expiration valve and increasing the rate of flow by a second increment when the second threshold value of the load situation of the expiration valve is exceeded.

2. A process in accordance with claim 1, wherein the monitoring of the load situation of the expiration valve and the reduction of the rate of flow is carried out synchronously with a continuous sequence of respiration cycles from one respiration cycle to the respective next respiration cycle or synchronously with the further sequence of subsequent respiration cycles.

3. A process in accordance with claim 1, wherein the monitoring of the load situation of the expiration valve and the increase in the rate of flow is performed synchronously with a continuous sequence of respiration cycles from one respiration cycle to the respective next respiration cycle or synchronously with the further sequence of subsequent respiration cycles.

4. A process in accordance with claim 1, wherein the monitoring of the load situation of the expiration valve and the reduction of the rate of flow is performed asynchronously with a sequence of respiration cycles.

5. A process in accordance with claim 1, wherein the monitoring of the load situation of the expiration valve and the increase in the rate of flow is performed asynchronously with a sequence of respiration cycles.

6. A process in accordance with claim 1, wherein a negative pressure change amplitude is imposed by means of a suction nozzle.

7. A process in accordance with claim 1, wherein during monitoring of the load situation the load situation is derived from a desired set point of the expiration valve.

8. A process in accordance with claim 7, wherein the desired set point of the expiration valve is formed as a current set point.

9. A process in accordance with claim 1, wherein during monitoring of the load situation the load situation is derived from an actual value of an actuating current of the expiration valve.

10. A process in accordance with claim 1, wherein during monitoring of the load situation the load situation is derived from a change in a resistance of an energized coil of the expiration valve relative to a reference resistance value with the coil of the expiration valve not energized.

11. A process in accordance with claim 1, wherein during monitoring of the load situation the load situation is derived from a mutual induction voltage of the expiration valve.

12. A process in accordance with claim 1, wherein the load situation is derived from a temperature value of the expiration valve relative to a reference temperature point.

13. A process in accordance with claim 1, wherein a starting flow value is derived from a set of parameters comprising frequency, pressure amplitude, mean airway pressure and inspiratory:expiratory ratio.

14. A process in accordance with claim 1, wherein the first increment is derived from the parameters comprising frequency, pressure amplitude, mean airway pressure and inspiratory:expiratory ratio.

15. A process in accordance with claim 1, wherein the second increment is derived from the parameters comprising frequency, pressure amplitude, mean airway pressure and inspiratory:expiratory ratio.

16. A process in accordance with claim 1, wherein the second increment is derived from the first increment.

17. A process in accordance with claim 1, wherein the second increment is derived from a difference between the load situation of the expiration valve and the first threshold value.

18. A process in accordance with claim 1, wherein the first and/or second increment is derived from the load situation of the expiration valve and from a first and/or second threshold value and changed.

19. A process in accordance with claim 18, wherein the derivation and changing of the first and/or second increment takes place continually and the load situation of the expiration valve is regulated in relation to the first and/or second threshold value.

20. A process in accordance with claim 18, wherein the regulation and variation of the first and/or second increment takes place continually and the load situation of the expiration valve is regulated into a tolerance range.

21. A process for controlling a respirator with an expiration valve, the process comprising:
providing a patient feed line connected to a valve arrangement of the respirator, wherein the valve arrangement includes the expiration valve;
providing a respiration flow with a preset starting flow value;
providing an alternating pressure amplitude to the respiration flow in the patient feed line in the rhythm of a high frequency by control actions including controlling the valve arrangement;
reducing a flow value, of the respiration flow, step by step from the preset starting flow value;
determining a load situation of the expiration valve during the step of reducing; and
maintaining the load situation of the expiration valve in a tolerance range by controlling the flow value.

* * * * *